United States Patent
Kawamura

(10) Patent No.: US 12,310,777 B2
(45) Date of Patent: May 27, 2025

(54) SUBJECT INFORMATION ACQUISITION DEVICE, METHOD FOR OPERATING SUBJECT INFORMATION ACQUISITION DEVICE, AND NON-TRANSITORY COMPUTER READABLE MEDIUM

(71) Applicant: FUJIFILM Corporation, Tokyo (JP)

(72) Inventor: Takahiro Kawamura, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 409 days.

(21) Appl. No.: 17/388,833

(22) Filed: Jul. 29, 2021

(65) Prior Publication Data
US 2021/0353241 A1    Nov. 18, 2021

Related U.S. Application Data

(63) Continuation of application No. PCT/JP2020/002749, filed on Jan. 27, 2020.

(30) Foreign Application Priority Data

Feb. 1, 2019    (JP) .................................. 2019-016987

(51) Int. Cl.
*A61B 6/50*    (2024.01)
*A61B 6/00*    (2024.01)

(52) U.S. Cl.
CPC ................ *A61B 6/50* (2013.01); *A61B 6/482* (2013.01); *A61B 6/5217* (2013.01)

(58) Field of Classification Search
CPC .......... A61B 6/50; A61B 6/482; A61B 6/5217
See application file for complete search history.

(56) References Cited

U.S. PATENT DOCUMENTS

| 5,774,520 | A | * | 6/1998 | Bolotin | G01B 15/025 |
| | | | | | 378/53 |
| 5,898,753 | A | * | 4/1999 | Schick | G01T 1/20184 |
| | | | | | 378/54 |
| 6,233,473 | B1 | * | 5/2001 | Shepherd | A61B 6/482 |
| | | | | | 600/407 |

(Continued)

FOREIGN PATENT DOCUMENTS

| JP | 2004-147863 A | 5/2004 |
| JP | 2015-019789 A | 2/2015 |

(Continued)

OTHER PUBLICATIONS

An Office Action; "Decision of Refusal", mailed by the Japanese Patent Office on Jun. 28, 2022, which corresponds to Japanese Patent Application No. 2020-569610 and is related to U.S. Appl. No. 17/388,833; with English language translation.

(Continued)

*Primary Examiner* — Oommen Jacob
(74) *Attorney, Agent, or Firm* — Studebaker Brackett PLLC

(57) ABSTRACT

A body thickness distribution calculation unit calculates a body thickness distribution of the subject. A soft region specification unit specifies a soft region indicating a region of a soft part from a radiographic image. A subject information acquisition unit calculates the proportion of muscle and the proportion of fat in the soft region for each pixel using the body thickness distribution and a pixel value of the soft region.

15 Claims, 4 Drawing Sheets

(56) References Cited

U.S. PATENT DOCUMENTS

| | | | |
|---|---|---|---|
| 6,922,462 B2 * | 7/2005 | Acharya | A61B 6/405 378/98.12 |
| 7,664,298 B2 * | 2/2010 | Lang | A61B 6/505 382/128 |
| 10,499,865 B2 * | 12/2019 | Wilson | A61B 6/482 |
| 2006/0109953 A1 * | 5/2006 | Walter | A61B 6/482 378/5 |
| 2012/0232375 A1 * | 9/2012 | Zebaze | G06T 7/70 600/407 |
| 2015/0262387 A1 * | 9/2015 | Zebaze | G06T 7/12 382/128 |
| 2016/0140720 A1 * | 5/2016 | Naito | A61B 6/5211 382/132 |
| 2016/0235385 A1 * | 8/2016 | Enomoto | A61B 6/5282 |
| 2016/0287194 A1 * | 10/2016 | Nariyuki | A61B 6/4411 |
| 2016/0324580 A1 * | 11/2016 | Esterberg | A61B 34/10 |
| 2016/0354051 A1 * | 12/2016 | Enomoto | A61B 6/4241 |
| 2018/0263559 A1 | 9/2018 | Kawamura | |
| 2018/0325476 A1 | 11/2018 | Machida et al. | |
| 2018/0333121 A1 | 11/2018 | Kuwabara et al. | |
| 2018/0368729 A1 | 12/2018 | Wilson et al. | |

FOREIGN PATENT DOCUMENTS

| | | |
|---|---|---|
| JP | 2016-190009 A | 11/2016 |
| JP | 2016-220850 A | 12/2016 |
| JP | 2018-153605 A | 10/2018 |

OTHER PUBLICATIONS

An Office Action; "Notice of Reasons for Refusal", mailed by the Japanese Patent Office on Apr. 12, 2022, which corresponds to Japanese Patent Application No. 2020-569610 and is related to U.S. Appl. No. 17/388,833; with English language translation.

International Search Report issued in PCT/JP2020/002749; mailed Mar. 31, 2020.

International Preliminary Report on Patentability and Written Opinion issued in PCT/JP2020/002749; issued Jul. 27, 2021.

The extended European search report issued by the European Patent Office on Feb. 22, 2022, which corresponds to European Patent Application No. 20748998.0-1126 and is related to U.S. Appl. No. 17/388,833.

Communication pursuant to Article 94(3) EPC issued by the European Patent Office on Aug. 6, 2024, which corresponds to European Patent Application No. 20748998.0-1122 and is related to U.S. Appl. No. 17/388,833.

* cited by examiner

SUBJECT INFORMATION ACQUISITION DEVICE, METHOD FOR OPERATING SUBJECT INFORMATION ACQUISITION DEVICE, AND NON-TRANSITORY COMPUTER READABLE MEDIUM

CROSS-REFERENCE TO RELATED APPLICATIONS

This application is a Continuation of PCT International Application No. PCT/JP2020/002749 filed on 27 Jan. 2020, which claims priority under 35 U.S.C § 119(a) to Japanese Patent Application No. 2019-016987 filed on 1 Feb. 2019. The above application is hereby expressly incorporated by reference, in its entirety, into the present application.

BACKGROUND OF THE INVENTION

1. Field of the Invention

The present invention relates to a subject information acquisition device, a method for operating a subject information acquisition device, and a non-transitory computer readable medium that acquire subject information such as the proportion of muscle or the proportion of fat in a subject.

2. Description of the Related Art

In the medical field, diagnosis using radiographic images is performed. In the diagnosis using the radiographic images, in addition to the radiographic images, subject information obtained from the radiographic images is used. For example, the proportion of fat in the subject or the proportion of muscle in the subject is used as the subject information.

For example, the proportion of fat is described in JP2018-153605A (corresponding to US2018/0263559A1). In JP2018-153605A, a soft part image is generated from a plurality of radiographic images by an energy subtraction process, and the body thickness distribution of the subject is estimated from the soft part image and the imaging conditions in a case in which the radiographic images are acquired. Then, an approximate body thickness distribution approximated by a model corresponding to the human body is calculated from the body thickness distribution, and the distribution of the proportion of fat in the subject is calculated from the approximate body thickness distribution.

Further, the proportion of fat and the proportion of muscle are described in JP2015-19789A. In JP2015-19789A, the proportion of fat and the proportion of muscle in a certain region, for example, the entire soft region are calculated by a dual X-ray absorptiometry (DXA) method.

SUMMARY OF THE INVENTION

However, it is required to calculate not the proportion of fat and the proportion of muscle in the entire soft region as in JP2015-19789A, but the proportion of fat and the proportion of muscle for each pixel of the soft region in order to make an accurate diagnosis on the basis of the proportion of fat and the proportion of muscle.

An object of the invention is to provide a subject information acquisition device, a method for operating a subject information acquisition device, and a non-transitory computer readable medium that can calculate the proportion of muscle and the proportion of fat in a subject for each pixel.

According to the invention, there is provided a subject information acquisition device comprising a processor. The processor acquires radiographic images obtained by capturing images of a subject including a soft part, calculates a body thickness distribution of the subject, specifies a soft region indicating a region of the soft part from the radiographic images, and calculates a proportion of muscle and a proportion of fat in the soft region for each pixel using the body thickness distribution and a pixel value of the soft region.

Preferably, the processor calculates the proportion of muscle and the proportion of fat from a predetermined specific relationship between the body thickness distribution and the pixel value of the soft region. Preferably, the specific relationship changes depending on imaging conditions at a timing when the images of the subject are captured. Preferably, the processor displays a distribution of the proportion of muscle and a distribution of the proportion of fat on a display.

Preferably, the radiographic images are first and second radiographic images having different energy distributions, and the soft region is specified by performing a calculation between corresponding pixels of the first and second radiographic images.

Preferably, the first and second radiographic images are obtained by detecting radiation transmitted through the subject with first and second radiation detectors that overlap each other while changing energy. Preferably, the first and second radiographic images are obtained by irradiating the subject with radiation having different energy distributions at different timings and detecting the radiation with one specific radiation detector. Preferably, the body thickness distribution is calculated by subtracting a source object distance (SOD) from a source image receptor distance (SID).

According to the invention, there is provided a method for operating a subject information acquisition device. The method includes processor implemented steps of: acquiring radiographic images obtained by capturing images of a subject including a soft part; calculating a body thickness distribution of the subject; specifying a soft region indicating a region of the soft part from the radiographic images; and calculating a proportion of muscle and a proportion of fat in the soft region for each pixel using the body thickness distribution and a pixel value of the soft region.

According to the invention, there is provided a non-transitory computer readable medium for storing a computer-executable program for causing a computer to perform steps of: acquiring radiographic images obtained by capturing images of a subject including a soft part; calculating a body thickness distribution of the subject; specifying a soft region indicating a region of the soft part from the radiographic images; and calculating a proportion of muscle and a proportion of fat in the soft region for each pixel using the body thickness distribution and a pixel value of the soft region.

According to the invention, it is possible to calculate the proportion of muscle and the proportion of fat in the subject for each pixel.

DESCRIPTION OF THE PREFERRED EMBODIMENTS

Figure 1:
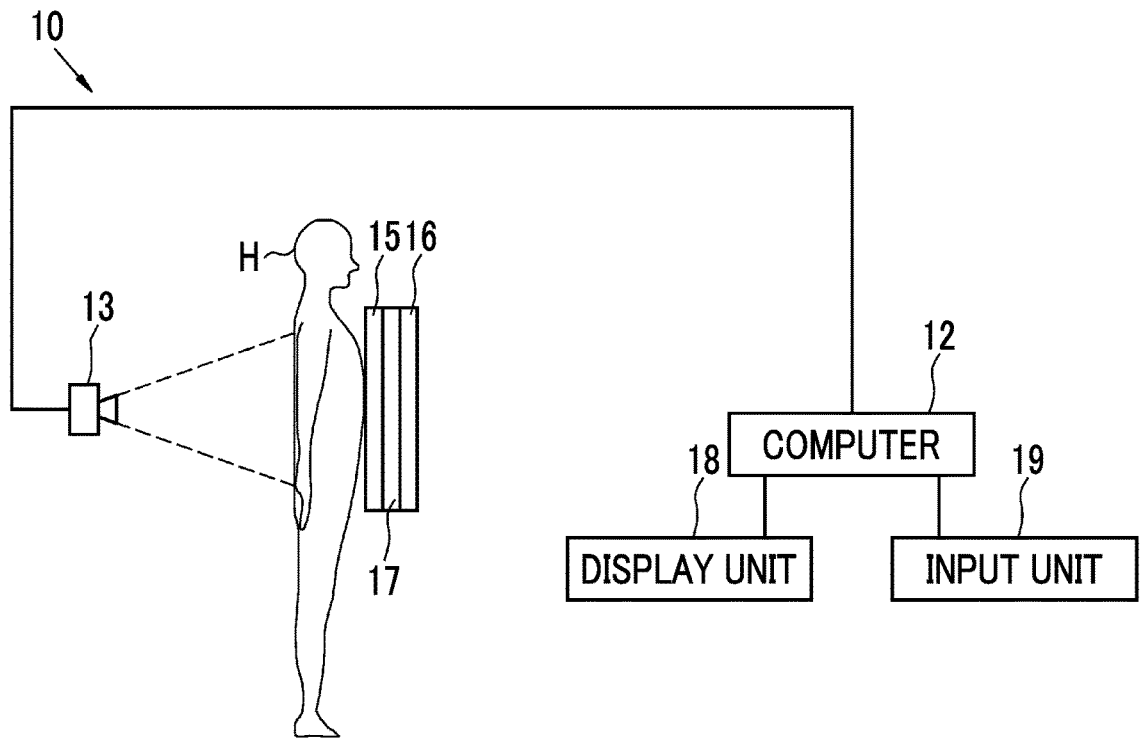
FIG. 1 is a diagram schematically illustrating a configuration of a radiography system.

As illustrated in FIG. 1, a radiography system comprises an imaging apparatus 10 and a computer 12, captures two radiographic images having different energy distributions, and acquires the proportion of muscle and fat using the two radiographic images. In the imaging apparatus 10, in a case in which a first radiation detector 15 and a second radiation detector 16 receive X-rays that have been emitted from an X-ray source 13 which is a radiation source and then transmitted through a subject H, the first radiation detector 15 and the second radiation detector 16 receive the X-rays while changing energy (one-shot energy subtraction). At the time of imaging, the first radiation detector 15, an X-ray energy conversion filter 17 that consists of, for example, a copper plate and the second radiation detector 16 are disposed in this order from the side closer to the X-ray source 13, and the X-ray source 13 is driven. In addition, the first and second radiation detectors 15 and 16 and the X-ray energy conversion filter 17 come into close contact with each other.

Therefore, the first radiation detector 15 obtains a first radiographic image G1 of the subject H formed by low-energy X-rays including so-called soft rays. In addition, the second radiation detector 16 obtains a second radiographic image G2 of the subject H formed by high-energy X-rays excluding soft rays. The first and second radiographic images G1 and G2 are input to the computer 12. In this embodiment, in a case in which a scattered ray removal grid that removes scattered ray components of the X-rays transmitted through the subject H is used at the time of capturing the image of the subject H, the first radiographic image G1 and the second radiographic image G2 include primary ray components of the X-rays transmitted through the subject H. On the other hand, in a case in which the scattered ray removal grid is not used at the time of capturing the image of the subject H, the first and second radiographic images G1 and G2 include primary ray components and scattered ray components of the X-rays.

A so-called direct-type radiation detector that can repeatedly perform the recording and reading of a radiographic image, directly receives the emitted radiation, and generates charge may be used as the first and second radiation detectors 15 and 16. Alternatively, an indirect radiation detector that converts radiation into visible light and then converts the visible light into a charge signal may be used as the first and second radiation detectors 15 and 16. A so-called optical reading method which turns on and off a thin film transistor (TFT) switch to read a radiographic image signal is preferably used as a radiographic image signal reading method.

A display unit 18 composed of a display and an input unit 19 are connected to the computer 12. The display unit 18 consists of a cathode ray tube (CRT), a liquid crystal display, or the like and displays a radiographic image or the like acquired by imaging. The input unit 19 consists of, for example, a keyboard, a mouse, or a touch panel.

A subject information acquisition program is installed in the computer 12. In this embodiment, the computer 12 may be a workstation or a personal computer that is directly operated by an operator, or a server computer that is connected to them through a network. The subject information acquisition program is recorded on a recording medium, such as a digital versatile disc (DVD) or a compact disc read only memory (CD-ROM), is distributed, and is then installed in the computer 12 from the recording medium. Alternatively, the subject information acquisition program is stored in a storage device of the server computer connected to the network or a network storage in a state in which it can be accessed from the outside and is downloaded and installed in the computer 12 as required.

Figure 2:
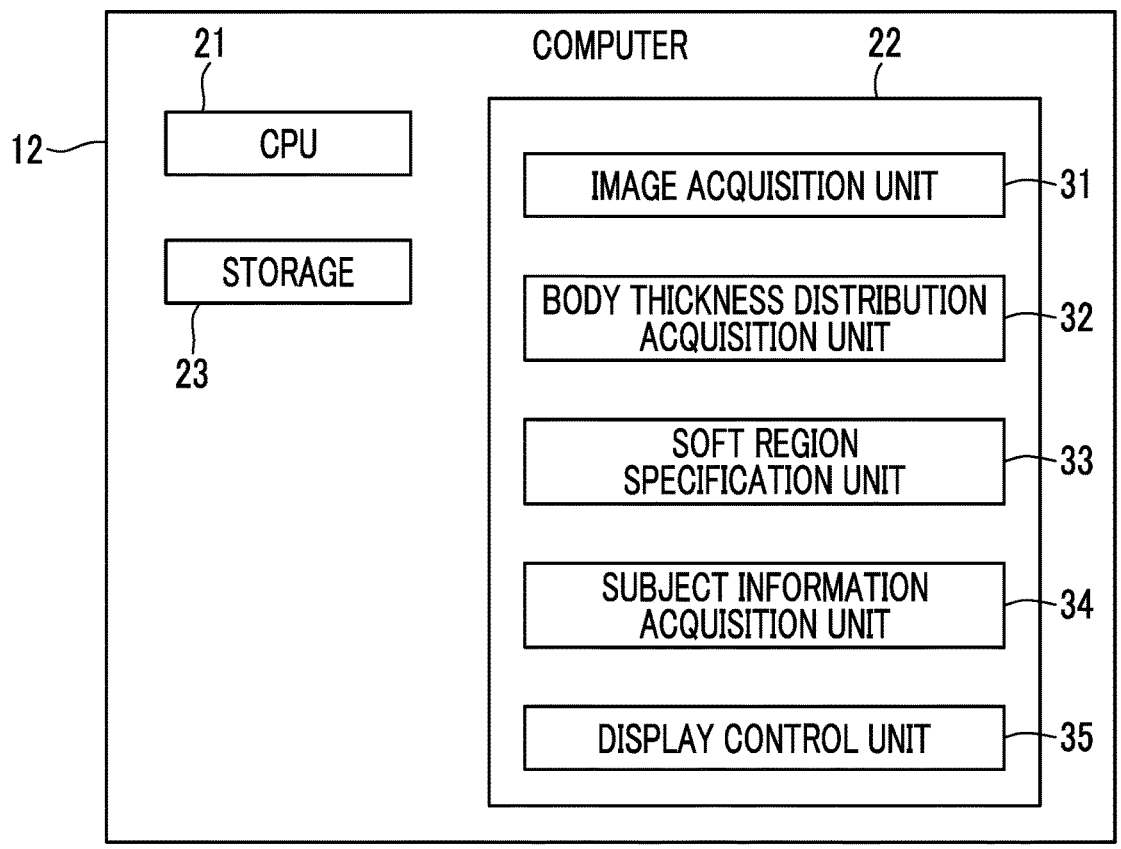
FIG. 2 is a block diagram illustrating the functions of a computer.

FIG. 2 illustrates a schematic configuration of a subject information acquisition device implemented by installing the subject information acquisition program in the computer 12. The subject information acquisition device comprises a central processing unit (CPU) 21, a memory 22, and a storage 23. The storage 23 consists of a storage device, such as a hard disk or a solid state drive (SSD), and stores various kinds of information including a program for driving each unit of the imaging apparatus 10 and an subject information acquisition program. In addition, the radiographic image acquired by imaging is stored in the storage 23.

The memory 22 temporarily stores, for example, the programs that are stored in the storage 23 in order to cause the CPU 21 to perform various processes. The subject information acquisition program defines the following processes as the processes to be performed by the CPU 21: an image acquisition process of directing the imaging apparatus 10 to perform imaging and acquiring the first and second radiographic images G1 and G2 as radiographic images; a body thickness distribution acquisition process of calculating a body thickness distribution of the subject; a soft region specification process of specifying a soft region from the radiographic images; a subject information acquisition process of calculating the proportion of muscle and the proportion of fat in the soft region using the body thickness distribution and a pixel value of the soft region; and a display control process of displaying subject information on the display unit 18. In addition, the subject information acquisition program includes a recognition process for specifying a soft region, which will be described below.

Then, the CPU 21 composed of a processor performs the processes according to the subject information acquisition program such that the computer 12 functions as an image acquisition unit 31, a body thickness distribution acquisition unit 32, a soft region specification unit 33, a subject information acquisition unit 34, and a display control unit 35. In addition, the computer 12 functions as a soft region recognition processing unit 40 (see FIG. 8). Further, in this embodiment, the CPU 21 implements the functions of each unit according to the subject information acquisition program. However, in addition to the CPU 21, a programmable logic device (PLD) that is a processor whose circuit configuration can be changed after manufacture, such as a field programmable gate array (FPGA), can be used as a general-purpose processor that executes software to function as various processing units. In addition, the processes of each unit may be performed by, for example, a dedicated electric circuit that is a processor having a dedicated circuit configuration designed to perform a specific process, such as an application specific integrated circuit (ASIC).

One processing unit may be configured by one of the various processors or a combination of two or more processors of the same type or different types (for example, a combination of a plurality of FPGAs or a combination of a CPU and an FPGA). Further, a plurality of processing units may be configured by one processor. A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as the hardware structure.

In addition, specifically, an electric circuit (circuitry) obtained by combining circuit elements, such as semiconductor elements, is used as the hardware structure of the various processors.

The image acquisition unit 31 acquires the first and second radiographic images G1 and G2 detected by the first and second radiation detectors 15 and 16. In this embodiment, the images of the abdomen of the subject H are captured from the chest, and the first and second radiographic images G1 and G2 of the abdomen from the chest are acquired. In this case, imaging conditions, such as an imaging dose, a tube voltage, a source image receptor distance (SID) which is a distance between the X-ray source 13 and the surfaces of the first and second radiation detectors 15 and 16, a source object distance (SOD) which is a distance between the X-ray source 13 and the surface of the subject H, and the presence or absence of the scattered ray removal grid, are set.

The SOD and the SID are used to calculate the body thickness distribution, which will be described below. It is preferable that the SOD is acquired by, for example, a time-of-flight (TOF) camera. It is preferable that the SID is acquired by, for example, a potentiometer, an ultrasonic range finder, or a laser range finder.

It is preferable that the imaging conditions are set by input from the input unit 19 by the operator. The set imaging conditions are stored in the storage 23. In addition, the acquisition program may acquire the first and second radiographic images G1 and G2 using a separate program and store the acquired radiographic images in the storage 23. In this case, the image acquisition unit 31 reads the first and second radiographic images G1 and G2 stored in the storage 23 from the storage 23 in order to process the radiographic images.

The body thickness distribution acquisition unit 32 calculates the body thickness distribution of the subject H on the basis of the SID and the SOD included in the imaging conditions. It is preferable that the body thickness distribution is calculated by subtracting the SOD from the SID. Further, the body thickness distribution is calculated for each pixel corresponding to the first and second radiographic images G1 and G2. Furthermore, instead of calculating the body thickness distribution on the basis of the SID and the SOD, the body thickness distribution may be calculated from at least one of the first radiographic image G1 or the second radiographic image G2. Moreover, the body thickness distribution may be calculated from the soft part image of the subject H obtained by performing weighting and subtraction between the corresponding pixels of the first radiographic image and the second radiographic image. In addition, in the calculation of the body thickness distribution, in a case in which the first and second radiation detectors 15 and 16 are provided in an imaging table (not illustrated) on which the subject H is placed, it is preferable that the distance of the X-ray source 13 to the surface of the imaging table which comes into contact with the subject H is used as the SID.

Figure 3:
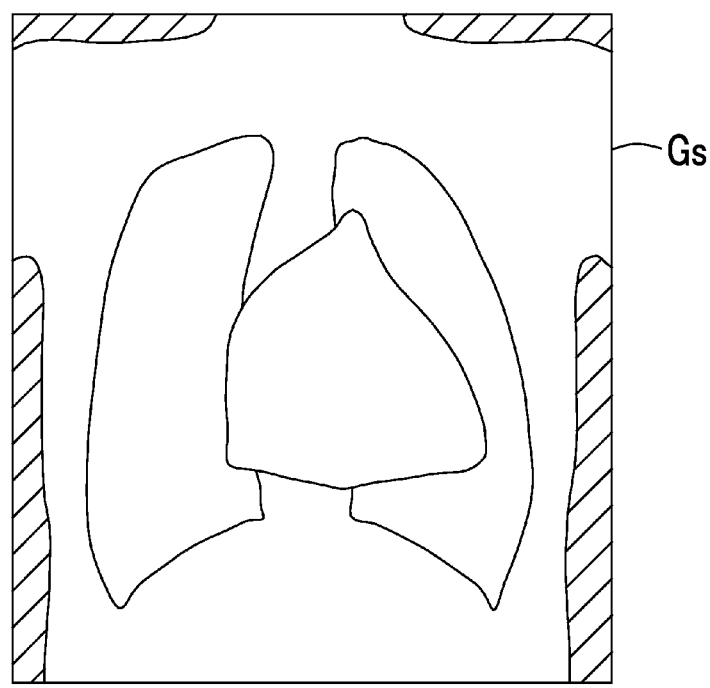
FIG. 3 is an image diagram illustrating a soft part image.

The soft region specification unit 33 specifies a soft region of the subject H from the first and second radiographic images G1 and G2. Specifically, the soft region specification unit 33 performs calculation, for example, weighting and subtraction between the corresponding pixels of the first and second radiographic images G1 and G2 as represented by the following Expression (1) to generate a soft part image Gs obtained by extracting only the soft region of the subject H included in each of the radiographic images G1 and G2 as illustrated in FIG. 3 (energy subtraction). In Expression (1), μ is a weighting coefficient. In addition, the pixel value of each pixel in the soft region of the soft part image Gs is a soft part pixel value.

$$Gs(x,y)=G1(x,y)-\mu \times G2(x,y) \quad (1)$$

Figure 4:
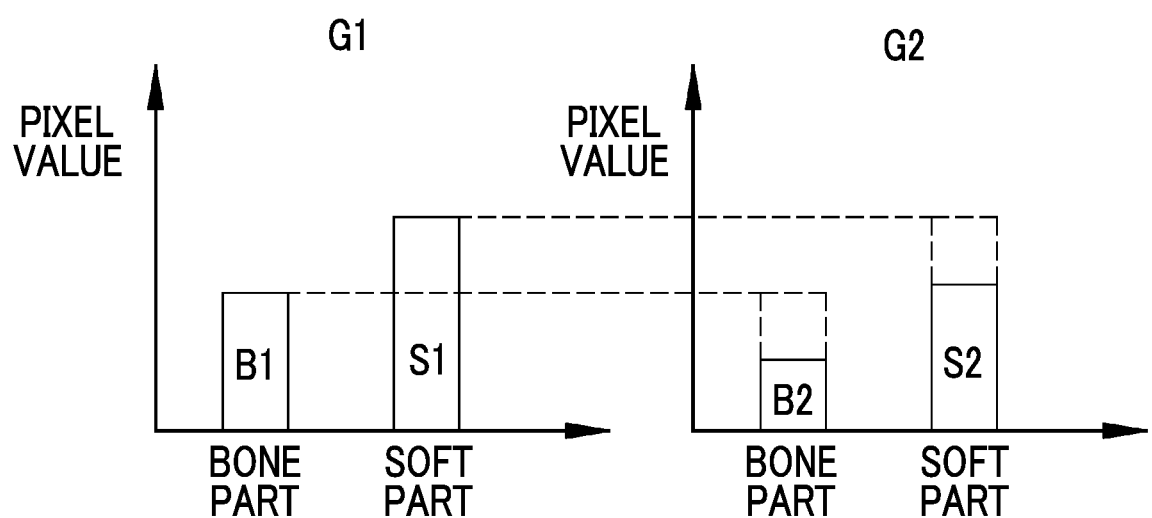
FIG. 4 is a diagram illustrating pixel values of a bone part and a soft part in first and second radiographic images G1 and G2.

For example, in a case in which the pixel value of a bone part and the pixel value of a soft part in the first radiographic image G1 are B1 and S1, respectively, and the pixel value of the bone part and the pixel value of the soft part in the second radiographic image G2 are B2 and S2, respectively, as illustrated in FIG. 4, in the obtainment of the soft part image Gs, the second radiographic image G2 is multiplied by the weighting coefficient μ in Expression (1) to make the pixel values of the bone part almost equal to each other in the first radiographic image G1 and the second radiographic image G2. Then, the second radiographic image G2 multiplied by the weighting coefficient is subtracted from the first radiographic image G1 to obtain the soft part image Gs obtained by extracting only the soft part.

In addition, for reference, a bone part image Gb obtained by extracting only the bone part from the first radiographic image G1 and the second radiographic image G2 may be generated. In this case, the second radiographic image G2 is multiplied by the weighting coefficient μ in Expression (1) to make the pixel values of the soft part almost equal to each other in the first radiographic image G1 and the second radiographic image G2. Then, the second radiographic image G2 multiplied by the weighting coefficient is subtracted from the first radiographic image G1 to obtain the bone part image Gb obtained by extracting only the bone part.

The subject information acquisition unit 34 acquires, as subject information related to the subject H, the proportion of muscle and the proportion of fat in the soft region for each pixel of the soft region included in the first and second radiographic images G1 and G2 on the basis of the body thickness distribution and the pixel value of the soft region. Specifically, the subject information acquisition unit 34 calculates the proportion of muscle and the proportion of fat from a predetermined specific relationship based on the body thickness distribution and the pixel value of the soft region. In addition, it is preferable that the specific relationship is stored by, for example, a look-up table (LUT).

Figure 5:
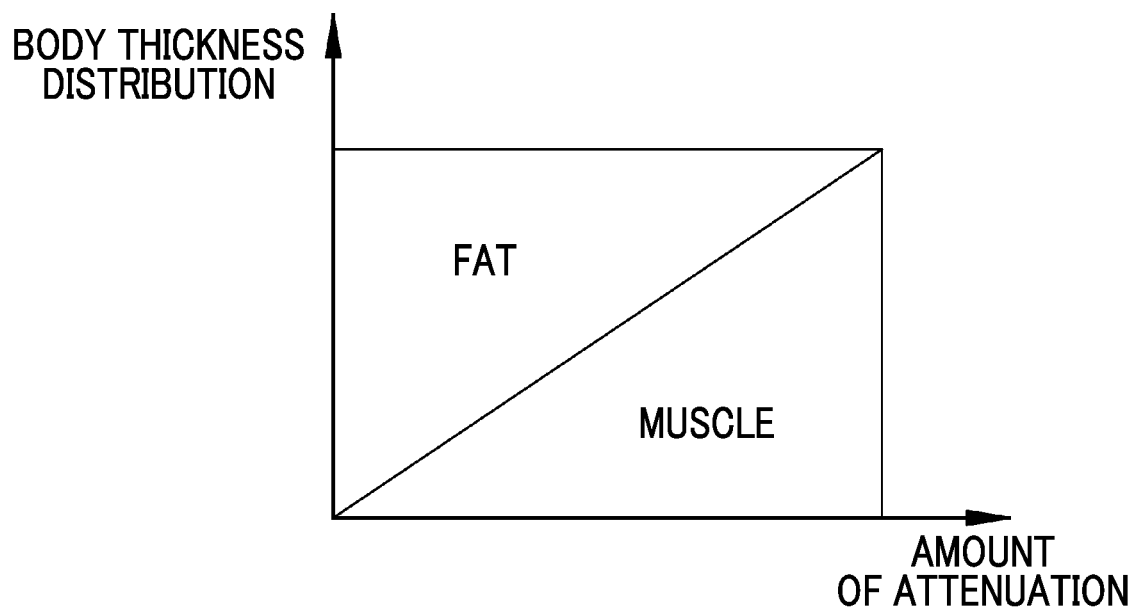
FIG. 5 is a diagram illustrating a specific relationship.

For example, for the specific relationship, in a case in which the body thickness distribution is represented by the vertical axis and the amount of attenuation (1/(the pixel value of the soft region)) indicating the reciprocal of the pixel value of the soft region is represented by the horizontal axis, it is preferable that the body thickness distribution and the amount of attenuation have the relationship illustrated in FIG. 5. In FIG. 5, as the body thickness distribution and the body thickness become larger, the proportion of fat becomes higher than the proportion of muscle. This takes advantage of the fact that the body thickness and fat are proportional to each other. In addition, as the amount of attenuation becomes larger, the proportion of muscle becomes higher than the proportion of fat. This takes advantage of the fact that the amount of attenuation of X-rays in muscle is larger than the amount of attenuation of X-rays in fat.

Further, it is preferable to change the specific relationship depending on the imaging conditions obtained at the timing when the image of the subject is captured, that is, the timing when the first radiographic image G1 or the second radiographic image G2 is acquired. For example, the amount of attenuation of X-rays in fat and muscle is changed by a change in the tube voltage or the dose of X-rays among the imaging conditions. Therefore, it is preferable to change the specific relationship according to a change in, for example, the tube voltage or the dose of X-rays. In a case in which the specific relationship is stored in the LUT, it is preferable to determine the specific relationship for each imaging condition.

Figure 6:
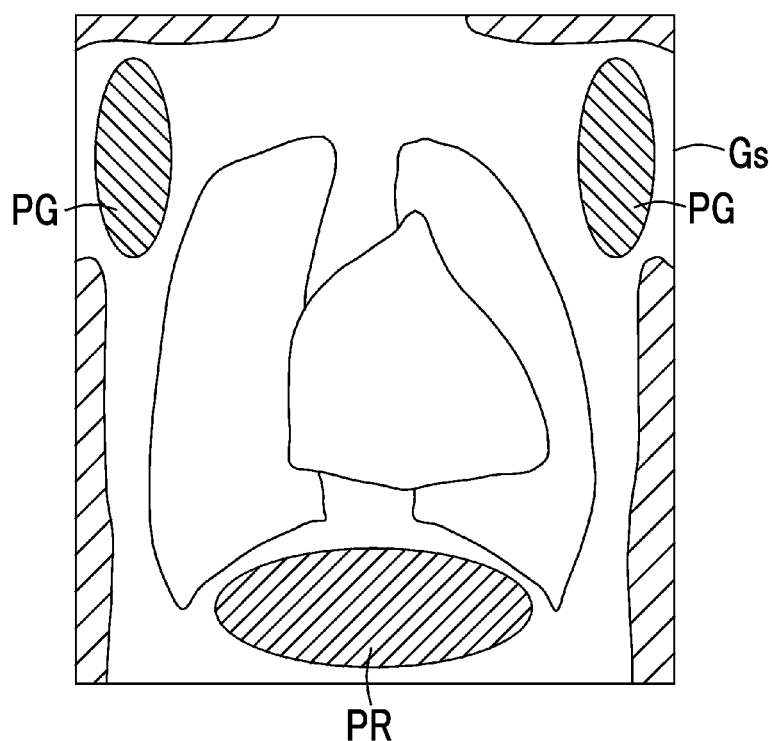
FIG. 6 is an image diagram illustrating a soft part image in which the proportion of muscle and the proportion of fat are displayed in pseudo-colors.

The display control unit 35 displays various kinds of information related to the subject H on the display unit 18. In a case in which the proportion of muscle and the proportion of fat are calculated as the subject information, it is preferable that muscle and fat proportion information corresponding to the distribution of the proportion of muscle and the distribution of the proportion of fat is displayed so as to be superimposed on the soft part image Gs. For example, in a case in which the muscle and fat proportion information is displayed in pseudo-colors corresponding to the distribution of the proportion of muscle and the distribution of the proportion of fat, as illustrated in FIG. 6, a portion in which the proportion of muscle is high may be represented by green PG, and a portion in which the proportion of fat is high may be represented by red PR in the soft part image Gs. Further, in addition to the soft part image Gs, the bone part image Gb or a composite image Gc of the soft part image Gs and the bone part image Gb may be used as the image on which the distributions of the proportions of muscle and fat are superimposed.

Figure 7:
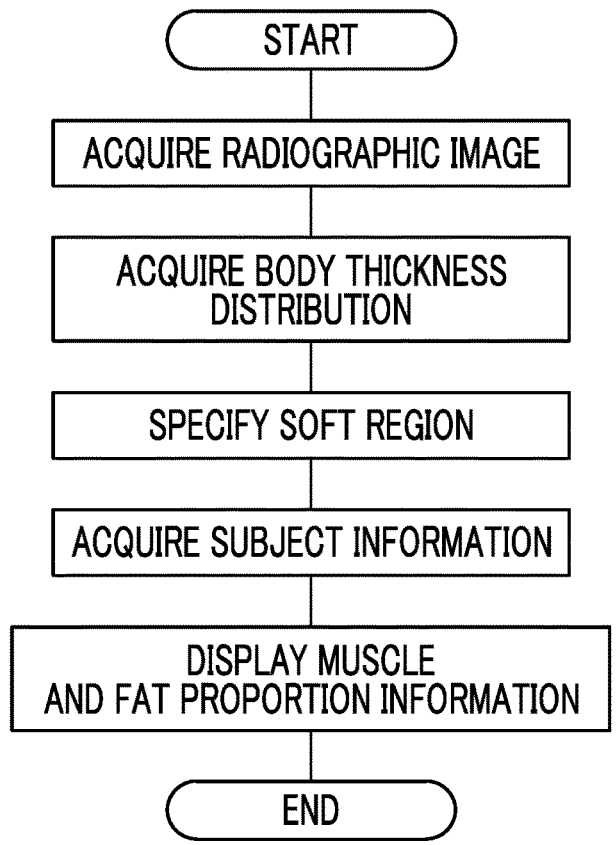
FIG. 7 is a flowchart illustrating a series of flows of the invention.

Next, a process performed in this embodiment will be described with reference to a flowchart illustrated in FIG. 7. The image acquisition unit 31 acquires the radiographic images obtained by capturing the images of the subject H irradiated with X-rays. It is preferable to acquire the first and second radiographic images G1 and G2 having different energy distributions as the radiographic images.

The body thickness distribution acquisition unit 32 acquires the body thickness distribution of the subject H. It is preferable to acquire the SID and the SOD and to subtract the SOD from the SID to acquire the body thickness distribution as a method for acquiring the body thickness distribution. Then, the soft region specification unit 33 specifies a soft region included in the subject H from the radiographic images. In a case in which the first and second radiographic images G1 and G2 are acquired as the radiographic images, it is preferable to specify the soft region using energy subtraction for the first and second radiographic images G1 and G2 (Expression (1)).

Then, the subject information acquisition unit 34 calculates the proportion of muscle and the proportion of fat in the soft region on the basis of the body thickness distribution and the pixel value of the soft region. The subject information acquisition unit 34 calculates the proportion of muscle and the proportion of fat from a predetermined specific relationship based on the body thickness distribution and the pixel value of the soft region. Then, the display control unit 35 displays muscle and fat proportion information corresponding to the proportion of muscle and the proportion of fat on the display unit 18 so as to be superimposed on an image such as the soft part image Gs.

Figure 8:
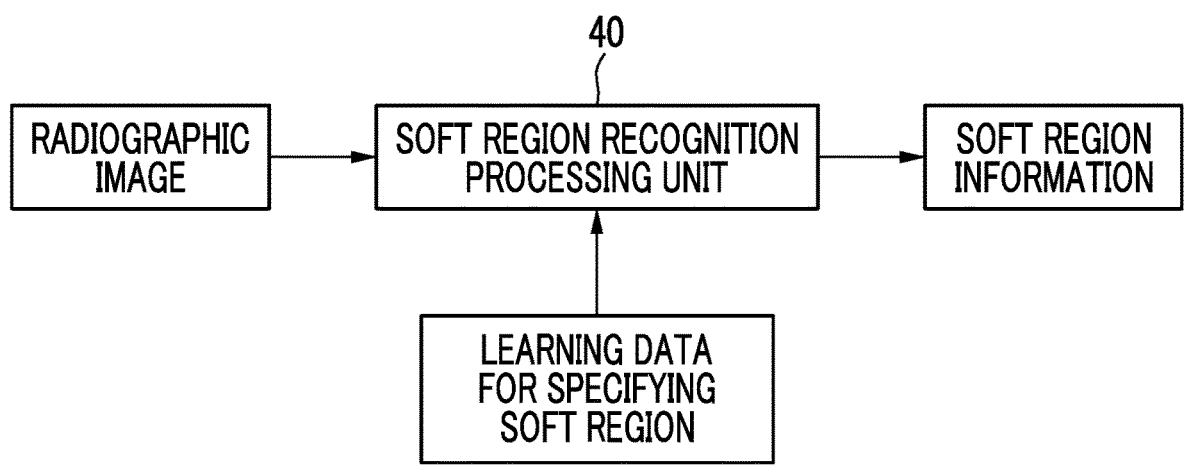
FIG. 8 is a diagram illustrating a soft region recognition processing unit.

Further, in the above-described embodiment, the soft region is specified by energy subtraction for the first and second radiographic images G1 and G2 having different energy distributions. However, the soft region may be specified by other methods. For example, as illustrated in FIG. 8, the soft region recognition processing unit 40 may perform the recognition process for specifying a soft region on one radiographic image having specific energy to specify the soft region (the output of information related to the soft region (soft region information)). In this case, it is preferable that the soft region recognition processing unit 40 is trained with learning data for specifying a soft region. For example, it is preferable to use a radiographic image, in which a soft region is specified by hatching or the like, as the learning data for specifying a soft region. In addition, similarly, it is preferable to perform a recognition process for specifying a bone region in a case in which the bone region is specified.

Further, a filtering process for specifying a soft region may be performed on one radiographic image to specify the soft region. For example, in a case in which there is a specific spatial frequency peculiar to a soft region, it is preferable to specify the soft region using a frequency filtering process that extracts a specific spatial frequency range. Alternatively, in a case in which the soft region has many low-frequency regions and it is difficult to specify the soft region using a frequency filtering process for extracting a soft region, the soft region may be specified by performing a frequency filtering process for extracting a bone region with a higher frequency than the soft region on a radiographic image and subtracting the radiographic image subjected to the frequency filtering process from the original radiographic image.

In the above-described embodiment, the first and second radiographic images G1 and G2 are acquired by the one-shot energy subtraction. However, the first and second radiographic images G1 and G2 may be acquired by a two-shot method that irradiates the subject with radiation having different energy distributions at different timings and detects the radiation with one specific radiation detector. In the two-shot method, any one of the imaging conditions in a case in which the first radiographic image G1 is acquired or the imaging conditions in a case in which the second radiographic image G2 is acquired may be used. Further, in the two-shot method, the position of the subject H included in the first and second radiographic images G1 and G2 is likely to be shifted by the body movement of the subject H. Therefore, it is preferable to align the subject in the first radiographic image G1 and the second radiographic image G2.

For example, a plurality of first band images and a plurality of second band images indicating structures having different frequency bands are generated for each of first and second radiographic images G1 and G2, and the amount of positional deviation between the corresponding positions in the first band image and the second band image of the corresponding frequency band is acquired. Then, the registration between the first radiographic image G1 and the second radiographic image G2 is performed on the basis of the amount of positional deviation.

EXPLANATION OF REFERENCES

10: imaging apparatus
12: computer
13: X-ray source
15: first radiation detector
16: second radiation detector
17: X-ray energy conversion filter
18: display unit
19: input unit
21: CPU
22: memory
23: storage
31: image acquisition unit
32: body thickness distribution acquisition unit
33: soft region specification unit
34: subject information acquisition unit
35: display control unit
40: soft region recognition processing unit
H: subject
G1: first radiographic image
G2: second radiographic image
Gs: soft part image

What is claimed is:

1. A subject information acquisition device comprising:
a processor,
wherein the processor
acquires a look-up table (LUT) that stores a relationship between a predetermined body thickness of a soft region composed of at least one of muscle and fat, an amount of attenuation of radiation represented by a pixel value of a radiographic image or a reciprocal of the pixel value at the predetermined body thickness of the soft region, and a proportion of muscle to fat corresponding to the amount of attenuation of radiation at the predetermined body thickness of the soft region;
acquires radiographic images of a subject and the body thickness corresponding to each pixel of the radiographic images of the subject; and
refers to the acquired LUT to calculate the proportion of muscle to fat corresponding to the pixel value of each pixel of the subject,
wherein the radiographic images are first and second radiographic images having different energy distributions, and
wherein the soft region is specified by performing a calculation between corresponding pixels of the first and second radiographic images.

2. The subject information acquisition device according to claim 1,
wherein the processor refers to the LUT according to imaging conditions depending on the imaging conditions at a timing when the images of the subject are captured.

3. The subject information acquisition device according to claim 1,
wherein the processor displays a distribution of the proportion of muscle and a distribution of the proportion of fat on a display.

4. The subject information acquisition device according to claim 1,
wherein the first and second radiographic images are obtained by detecting radiation transmitted through the subject with first and second radiation detectors that overlap each other, each detecting at different energies.

5. The subject information acquisition device according to claim 1,
wherein the first and second radiographic images are obtained by irradiating the subject with radiation having different energy distributions at different timings and detecting the radiation with one specific radiation detector.

6. The subject information acquisition device according to claim 1,
wherein the body thickness corresponding to each pixel of the radiographic images of the subject is calculated by subtracting a source object distance (SOD) from a source image receptor distance (SID).

7. A method for operating a subject information acquisition device,
the method comprising processor implemented steps of:
acquiring a look-up table (LUT) that stores a relationship between a predetermined body thickness of a soft region composed of at least one of muscle and fat, an amount of attenuation of radiation represented by a pixel value of a radiographic image or a reciprocal of the pixel value at the predetermined body thickness of the soft region, and a proportion of muscle to fat corresponding to the amount of attenuation of radiation at the predetermined body thickness of the soft region;
acquiring radiographic images of a subject and the body thickness corresponding to each pixel of the radiographic images of the subject; and
referring to the acquired LUT to calculate the proportion of muscle to fat corresponding to the pixel value of each pixel of the subject,
wherein the radiographic images are first and second radiographic images having different energy distributions, and
wherein the soft region is specified by performing a calculation between corresponding pixels of the first and second radiographic images.

8. A non-transitory computer readable medium for storing a computer-executable program for acquiring subject information, the computer-executable program causing a computer to perform steps of:
acquiring a look-up table (LUT) that stores a relationship between a predetermined body thickness of a soft region composed of at least one of muscle and fat, an amount of attenuation of radiation represented by a pixel value of a radiographic image or a reciprocal of the pixel value at the predetermined body thickness of the soft region, and a proportion of muscle to fat corresponding to the amount of attenuation of radiation at the predetermined body thickness of the soft region;
acquiring radiographic images of a subject and the body thickness corresponding to each pixel of the radiographic images of the subject; and
referring to the acquired LUT to calculate the proportion of muscle to fat corresponding to the pixel value of each pixel of the subject,
wherein the radiographic images are first and second radiographic images having different energy distributions, and
wherein the soft region is specified by performing a calculation between corresponding pixels of the first and second radiographic images.

9. A radiography system comprising:

a radiation source that emits radiation;

a radiation detector that detects radiation transmitted through a subject and acquires a radiographic image of the subject; and a processor, wherein the processor acquires a look-up table (LUT) that stores a relationship between a predetermined body thickness of a soft region composed of at least one of muscle and fat, an amount of attenuation of radiation represented by a pixel value of a radiographic image or a reciprocal of the pixel value at the predetermined body thickness of the soft region, and a proportion of muscle to fat corresponding to the amount of attenuation of radiation at the predetermined body thickness of the soft region;

acquires radiographic images of a subject and the body thickness corresponding to each pixel of the radiographic images of the subject; and refers to the acquired LUT to calculate the proportion of muscle to fat corresponding to the pixel value of each pixel of the subject, wherein the radiographic images are first and second radiographic images having different energy distributions, and wherein the soft region is specified by performing a calculation between corresponding pixels of the first and second radiographic images.

10. The radiography system according to claim 9, wherein the processor refers to the LUT according to imaging conditions depending on the imaging conditions at a timing when the images of the subject are captured.

11. The radiography system according to claim 9, wherein the processor displays a distribution of the proportion of muscle and a distribution of the proportion of fat on a display.

12. The radiography system according to claim 9, wherein the radiographic images are first and second radiographic images having different energy distributions, and the soft region is specified by performing a calculation between corresponding pixels of the first and second radiographic images.

13. The radiography system according to claim 12, wherein the first and second radiographic images are obtained by detecting radiation transmitted through the subject with first and second radiation detectors that overlap each other, each detecting at different energies.

14. The radiography system according to claim 12, wherein the first and second radiographic images are obtained by irradiating the subject with radiation having different energy distributions at different timings and detecting the radiation with one specific radiation detector.

15. The radiography system according to claim 9, wherein the body thickness corresponding to each pixel of the radiographic images of the subject is calculated by subtracting a source object distance (SOD) from a source image receptor distance (SID).

* * * * *